United States Patent [19]
Reich

[11] 4,380,450
[45] Apr. 19, 1983

[54] SANITARY NAPKIN WITH DISPOSAL MEANS

[75] Inventor: Jack W. Reich, Neenah, Wis.

[73] Assignee: Kimberly-Clark Corporation, Neenah, Wis.

[21] Appl. No.: 276,917

[22] Filed: Jun. 24, 1981

[51] Int. Cl.³ .............................. A61F 13/16
[52] U.S. Cl. .................................... 604/386
[58] Field of Search ............... 128/284, 287, 290 R, 128/290 P, DIG. 30; 604/386–387, 389

[56] References Cited

U.S. PATENT DOCUMENTS

| | | | |
|---|---|---|---|
| 3,604,423 | 9/1971 | Fraser | 128/290 R |
| 3,967,622 | 7/1976 | Cepuritis | 128/DIG. 30 |
| 3,973,567 | 8/1976 | Srinivasan et al. | 128/290 R |
| 4,023,570 | 5/1977 | Chinai et al. | 128/DIG. 30 |
| 4,079,739 | 3/1978 | Whitehead | 128/290 R |
| 4,182,336 | 1/1980 | Black | 128/290 R |

*Primary Examiner*—C. Fred Rosenbaum
*Attorney, Agent, or Firm*—Howard Olevsky; William D. Herrick

[57] ABSTRACT

A sanitary napkin of otherwise conventional construction is provided with an adhesive on at least one end of the napkin at the body-facing side. The adhesive area is provided at a portion of the end extending beyond the absorbent layer and the wrap in this area is folded over to prevent attachment to the body.

2 Claims, 4 Drawing Figures

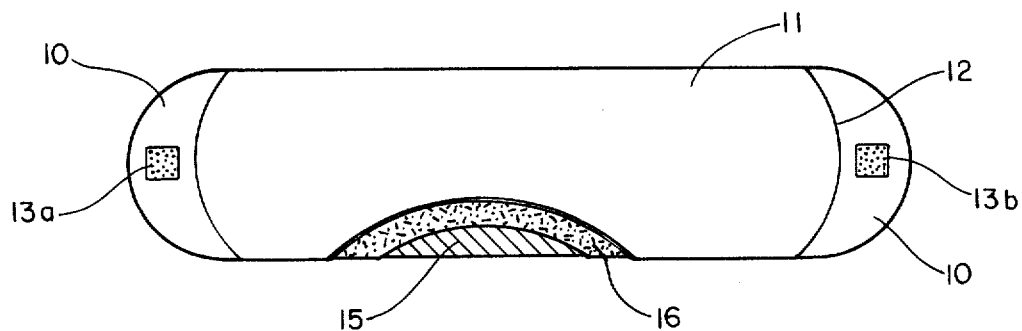
FIG. 1
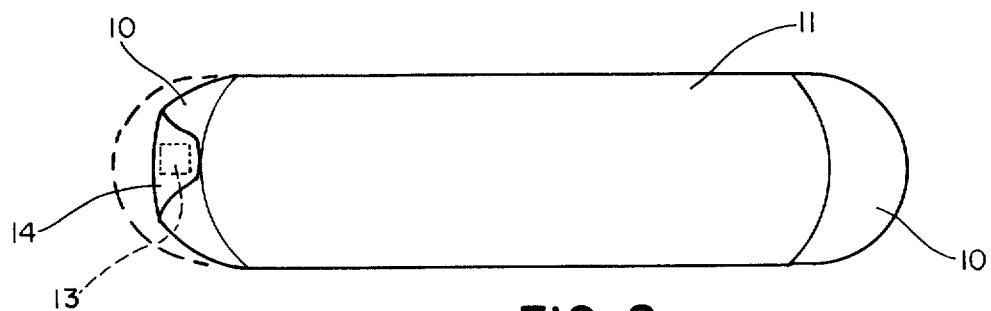
FIG. 2
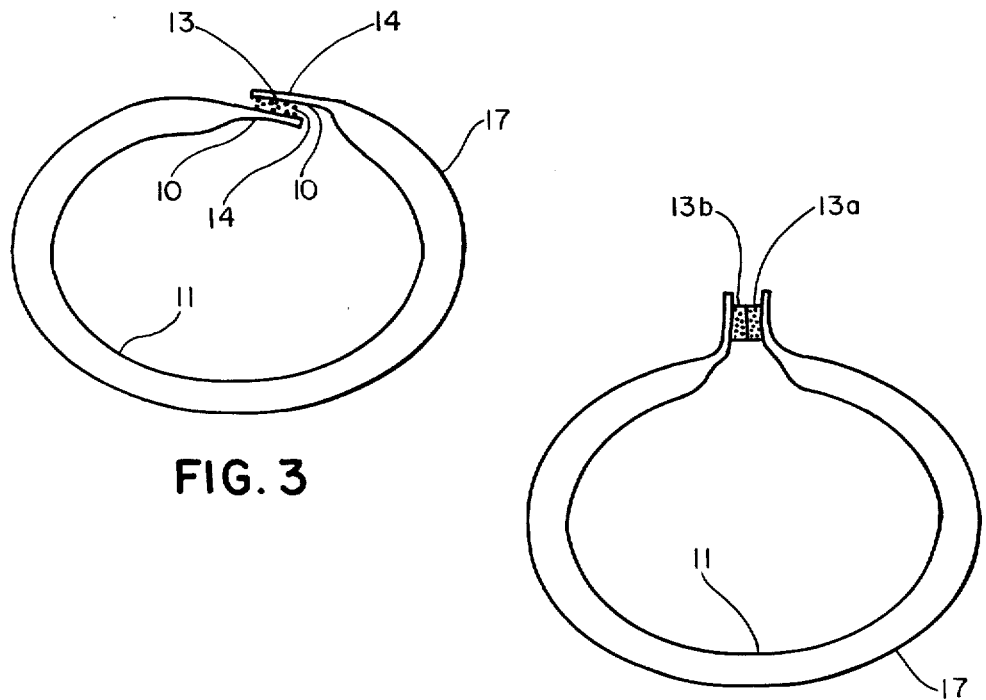
FIG. 3
FIG. 4

SANITARY NAPKIN WITH DISPOSAL MEANS

FIELD OF THE INVENTION

The subject invention relates to a sanitary napkin and particularly to a sanitary napkin with disposal means incorporated therewith.

BACKGROUND OF THE INVENTION

One of the problems associated with the use of sanitary napkins has been their disposal. Used napkins are unattractive and can be messy. Attempts to provide disposal aids have generally followed one of two directions. The first of these involves the use of a bag or bag-like attachment affixed to or as part of a sanitary napkin. Examples of various embodiments of this approach can be found in U.S. Pat. Nos. 4,182,336; 3,604,423 and 3,274,999.

The self-contained bag has been unsuccessful for a variety of reasons. The self-contained bag is on the bottom of the napkin and therefore must, by its nature, interfere with adhesive attachment of the napkin to the panty. Also, a napkin with such a self-contained bag is both expensive and difficult to manufacture.

Another alternative involves the utilization of adhesive areas at the longitudinal ends of the garment facing side of the napkin. These adhesive areas may be covered by an extension or an added element and after the napkin is used, it is rolled into a tightly wound cylinder with the adhesive tab being used to fasten the roll. This approach, while simpler from a manufacturing standpoint, still involves the use of a separate tab and the user of the napkin must touch the soiled napkin to be able to roll it. Also, extremely thick napkins are difficult to roll because of limited flexibility. The pressure involved in rolling a napkin can, in certain instances provide for fluid "strikeback" through the wrapper of the napkin. For this reason a disposal system of the type disclosed in U.S. Pat. No. 3,626,945 has met with little success.

U.S. Pat. Nos. 2,742,903 and 4,072,151 have a structure which places adhesive on the body-facing side of the sanitary napkin for direct attachment to the wearer.

SUMMARY OF THE INVENTION

According to this invention a sanitary napkin is provided having at least one adhesive area positioned at the longitudinal ends of the napkin beyond the absorbent layer on the side facing the wearer. The adhesive area is shielded from the wearer because the end of the napkin is folded over. After the napkin has been used and is ready to be discarded, the wearer opens the folded end and attaches the adhesive surface to the opposite end so that the napkin, when attached, resembles a circle. The used portion of the napkin is at least partially visually screened and there is virtually no compression of the absorbent layer involved in this attachment so strikeback is not a problem. Furthermore, the user does not have to touch the soiled portion of the napkin prior to disposal.

BRIEF DESCRIPTION OF THE DRAWINGS

The invention may more readily be understood by reference to the drawings in which FIG. 1 is a plan view partially in cross-section of one embodiment of the subject invention.

FIG. 2 is a plan view of a second embodiment.

FIG. 3 is an elevation of the embodiment of FIG. 2 showing the napkin ready for disposal and FIG. 4 is a side elevation of the napkin of FIG. 1 showing the napkin ready for disposal. (In all FIGS. like numbers denominate like elements.)

According to FIG. 1, a sanitary napkin having a fluid impermeable baffle 15, an absorbent layer 16 and a fluid pervious cover 11 overwrapping the entire napkin is shown. The napkin is sealed at the bottom or garment facing side by adhesive strips (not shown) which attach overlapped portions of the fluid permeable wrap to each other and also to provide suitable garment attachment means. This attachment system is well known and currently being used on commercially available products and is not part of the subject invention. This particular napkin is sealed as represented by line 12 near its ends. This sealing is done preferably by fusing and most preferably by ultrasonic fusing of the wrap to itself or to a baffle portion 15 extending to the ends of the napkin. The absorbent 16, as is conventional, does not extend beyond the fused line 12.

The napkin depicted in FIG. 1, has two adhesive areas 13a and 13b with the tab ends 10 in an open configuration exposing the adhesive areas and therefore ready for disposal. Referring to FIG. 4, the napkin is shown ready for disposal with the bottom surface of the wrap 17 shown as forming the outer part of the circle formed by the napkin due to the attachment of adhesive faces 13a and 13b. This particular configuration provides tab ends at the top of the circle for control by the fingers of the wearer. When adhesive to adhesive contact provides the sealing means the cohesive nature of the two adhesive areas must be sufficiently strong to overcome the natural resistance to deformation for a time sufficient to achieve disposal of the napkin.

The embodiment shown at FIG. 2 has an adhesive area 13 shown in dotted lines at only one end of the napkin. The embodiment depicted in FIG. 2 shows the end 10 folded over so that the bottom surface 14 of the end is directed toward the body of the wearer when the napkin is in place. As can be seen by reference to FIG. 3, in this particular instance, the adhesive surface 13 is applied to the bottom end 14 of the opposite side of the napkin. This sealing position is one possibility. It is also possible to seal to provide attachment to the body facing side 10 of the opposite flap 14 as shown in FIG. 4. Furthermore, attachment need not be precisely one end to another but may extend inward along the bottom surface. The particular position of attachment is not critical and may be governed by the napkin construction i.e. the thinner and more resilient the napkin the tighter the napkin can be drawn in a circle after attachment.

Variations of the concept of the subject invention will readily suggest themselves to those with reasonable skill in the art. The basic concept of the subject invention, simply stated, is the addition of an adhesive area to the body-facing side of a sanitary napkin and the folding of the ends of the napkin to shield the adhesive area from contact with the body of the wearer. This concept coupled with the unfolding of the ends and its subsequent adhesion to form a continuous outer napkin surface is the nexus of this invention.

What is claimed is:

1. A sanitary napkin with a body facing side and a garment facing side comprising a fluid impermeable baffle, an absorbent layer and a fluid pervious wrap positioned between the wearer and the absorbent layer, said wrap and said baffle extending beyond the longitudinal ends of the absorbent layer to form the flexible longitudinal ends of the napkin at least one of said napkin ends containing a discrete adhesive area on the body facing side and having garment attachment adhesive means on the garment facing side.

2. The napkins according to claim 1 wherein at least one of the flexible napkin ends is folded upon itself with the adhesive used to maintain the fold.